US00PP26506P3

(12) United States Plant Patent
Westphal

(10) Patent No.: US PP26,506 P3
(45) Date of Patent: Mar. 15, 2016

(54) ***CLEMATIS* PLANT NAMED 'PASSION PLUM'**

(50) Latin Name: *Clematis lanuginosa×patens*
Varietal Denomination: Passion Plum

(71) Applicant: Friedrich Manfred Westphal, Prisdorf (DE)

(72) Inventor: Friedrich Manfred Westphal, Prisdorf (DE)

( * ) Notice: Subject to any disclaimer, the term of this patent is extended or adjusted under 35 U.S.C. 154(b) by 99 days.

(21) Appl. No.: 14/120,186

(22) Filed: May 1, 2014

(65) Prior Publication Data

US 2015/0319896 P1 Nov. 5, 2015

(51) Int. Cl.
*A01H 5/02* (2006.01)

(52) U.S. Cl.
USPC ..... Plt./228

(58) Field of Classification Search
USPC ..... Plt./228
See application file for complete search history.

*Primary Examiner* — Susan McCormick Ewoldt
(74) *Attorney, Agent, or Firm* — Cassandra Bright

(57) ABSTRACT

A new and distinct *Clematis* cultivar named 'Passion Plum' is disclosed, characterized by short, very compact plant growth and a long, continuous flowering period from Spring through Summer. Flowers are distinctively colored dark pink with a darker pink bar. The new cultivar is a *Clematis*, suitable for ornamental garden purposes.

1 Drawing Sheet

Latin name of the genus and species: *Clematis lanuginosa×patens.*

Variety denomination: 'PASSION PLUM'.

BACKGROUND OF THE INVENTION

The new cultivar is a product of a planned breeding program conducted by the inventor during 2009. May of 2009, the inventor, Friedrich Manfred Westphal, a citizen of Germany, made a crossing of the seed parent *Clematis lanuginosa* 'Carnaby', unpatented, with the pollen parent, *Clematis patens* 'Rosa Konigskind', unpatented Seeds originating from this crossing were planted out, and the new variety was selected during 2010. All work was conducted at a commercial nursery in Prisdorf, Germany.

The inventor first propagated 'Passion Plum' by vegetative cuttings at the commercial nursery in Prisdorf, Germany in April of 2010. Subsequent generations have shown that the unique features of this cultivar are stable and reproduced true to type.

SUMMARY OF THE INVENTION

The cultivar 'Passion Plum' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Passion Plum' These characteristics in combination distinguish 'Passion Plum' as a new and distinct *Clematis* cultivar:

1. Very short, compact plant habit
2. Long flowering period, continuously throughout Summer
3. Distinctive dark pink flower, with a darker pink bar
4. Highly floriferous plant

COMPARISON TO PARENT VARIETY

Plants of the new cultivar 'Passion Plum' are similar to plants of the seed parent; *Clematis lanuginosa* 'Carnaby' in most horticultural characteristics, however, plants of the new cultivar 'Passion Plum' are shorter and more compact, and flower over a longer period. Additionally, plants of 'Passion Plum' produce flowers that are much darker pink.

Plants of the new cultivar 'Passion Plum' are similar to plants of the pollen parent; *Clematis patens* 'Rosa Konigskind' in most horticultural characteristics, however, plants of the new cultivar 'Passion Plum' are shorter and more compact. Additionally, plants of 'Passion Plum' produce flowers that are much darker colored than the pollen parent.

COMMERCIAL COMPARISON

'Passion Plum' can be compared to the commercial variety 'Dorami', U.S. Plant Pat. No. 21,740. 'Passion Plum' and 'Dorami' are similar in most horticultural characteristics, especially in compact plant habit and their continuous flowering characteristic. However, plants of 'Passion Plum' produce a dark pink and pink flower, compared to the purple flower of 'Dorami'

'Passion Plum' can also be compared to *Clematis* 'Jenmar' U.S. Plant Pat. No. 21,713. 'Passion Plum' and 'Jenmar' are similar in most horticultural characteristics, especially in compact plant habit and their continuous flowering characteristic. However, plants of 'Passion Plum' produce a dark pink and pink flower, compared to the purple flower of 'Jenmar'. Additionally, the petal aspect is much different between the varieties.

BRIEF DESCRIPTION OF THE PHOTOGRAPH

The accompanying photograph in FIG. 1 illustrates in full color a close up of typical foliage and flowers of 'Passion Plum' grown outdoors in Germany.

The plant is approximately 1 year old, and is planted in the ground. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Passion Plum' plants grown in a greenhouse in Prijsdorf, Germany. Plants are approximately 1 year old, in a 1 liter nursery container. The greenhouse is unheated and unshaded. Temperatures ranged from 2° C. to 20° C. at night to 5° C. to 35° C. during the day. Measurements and numerical values represent averages of typical plant types.

Botanical classification: *Clematis lanuginose×patens* 'Passion Plum'.

PROPAGATION

Time to rooting:

*Initiation*.—Approximately 22 days in the Summer at approximately 24° C.

*Rooted cuttings production*.—Approximately 55 days in the Summer at approximately 20° C. to 26° C.

Root description: Fine, fibrous.

PLANT

Growth habit: Climbing vine.

Height: Approximately 150 cm, measured from the soil line of the pot after approximately 1 year.

Plant spread: Approximately 45 cm to 60 cm after approximately 1 year.

Growth rate: During active growing season in Spring, approximately 20 to 30 cm per month.

Branching characteristics: One main stem, and 1 to 5 lateral branches, typically given a pinch.

Length of main stem: Approximately 180 cm.

Diameter of main stem: Approximately 0.8 cm.

Main stem color: Near RHS Green 137B, flushed Greyed-Red 178A.

Main stem texture: Slightly pubescent.

Internode length: Varies from 7 to 12 cm.

Strength: Strong, flexible, semi-woody.

FOLIAGE

Leaf:

*Type*.—Simple.

*Arrangement*.—Opposite.

*Leaves per lateral branch*.—Average 3.

*Average length*.—Approximately 5 to 6.5 cm.

*Average width*.—Approximately 3.5 to 4.5 cm.

*Shape of blade*.—Oblong.

*Apex*.—Acute.

*Base*.—Cordate.

*Margin*.—Entire.

*Texture of top surface*.—Smooth.

*Texture of bottom surface*.—Smooth.

*Leaf internode length*.—Approximately 2 cm.

*Color*.—Young foliage upper side: Near RHS Green 137C. Young foliage under side: Near RHS Green 137B. Mature foliage upper side: Near RHS Green 137A Mature foliage under side: Near RHS Green 137B.

*Venation*.—Type: Pinnate. Venation color upper side: Near RHS Green 137B. Venation color under side: Near RHS Green 137A.

*Petiole*.—Average Length: Approximately 5 to 7 cm. Color: Near RHS Greyed-Red 180B. Diameter: Approximately 0.2 cm. Texture: Smooth.

FLOWER

Bloom period:

*Natural season*.—Continuously from Spring through Summer.

Inflorescence type and habit: Single, axillary; flowers facing outward.

Flower longevity on plant: Approximately 10 days, after fully opened. Self-cleaning.

Quantity of flowers: Approximately 20 open flowers at one time. Approximately 3 to 5 per flowering stem.

Inflorescence size:

*Diameter*.—Approximately 10 to 14 cm.

*Depth*.—Approximately 2.0 cm.

Corolla:

*Tepal arrangement*.—Single whorl, slightly overlapping.

*Quantity*.—Approximately 6 per flower.

*Size*.—Length: Approximately 6 to 7 cm. Width: Approximately 2.5 cm.

*Margin*.—Entire, slightly undulating.

*Apex*.—Acute.

*Base*.—Truncate.

*Texture*.—Smooth, velvety.

Color:

*Tepals*.—When opening: Upper surface: Near RHS Red-Purple 72A, center near Red-Purple 71A. Lower surface: Near RHS Red-Purple 72A, center near Red-Purple 71A. Fully opened: Upper surface: Near RHS Red-Purple 70B, center near Red-Purple 71A. Lower surface: Near RHS Red-Purple 70B, center near Red-Purple 71A. Ageing: Upper Surface: Near RHS Red-Purple N74C, center near Red-Purple 61A. Lower Surface: Near RHS Red-Purple N74C, center near Red-Purple 61A.

Bud:

*Shape*.—Ovate.

*Length*.—Approximately 2 to 5 cm.

*Diameter*.—Approximately 1.5 to 2.5 cm.

*Color*.—Near RHS Red-Purple 72A, streaks near Red-Purple 71A.

Pedicels:

*Length*.—Approximately 4 to 10 cm.

*Width*.—Approximately 0.4 cm.

*Angle*.—Average 80°.

*Strength*.—Strong, flexible.

*Color*.—Near RHS Greyed-Orange 165C.

Fragrance: None.

REPRODUCTIVE ORGANS

Stamens:

*Number*.—Approximately 70 to 90 per flower.

*Anther length*.—0.8 cm 1.2 cm.

*Anther color*.—Near RHS Red-Purple 61A.

*Anther shape*.—Oblong.

*Pollen quantity*.—Not observed to date.

*Filament length*.—Approximately 1.2 to 2.0 cm.

*Filament aspect*.—Straight.

*Filament color*.—Near RHS Red-Purple 70B.

Pistil:

*Number*.—Approximately 30 to 50 per flower.

*Length*.—Approximately 0.8 cm.

*Style color*.—Near RHS Red-Purple 70B.

*Style length*.—Approximately 0.7 cm.

*Stigma*.—Shape: Linear. Color: Near RHS Red-Purple 70B.

OTHER CHARACTERISTICS

Seeds and fruits: Not observed to date.

Disease/pest resistance: Neither resistance nor susceptibility to pathogens and pests common to *Clematis* have been observed.

Temperature tolerance: Tolerates temperatures from approximately −20°C. to 45° C.

What is claimed is:

1. A new and distinct cultivar of *Clematis* plant named 'Passion Plum' as herein illustrated and described.

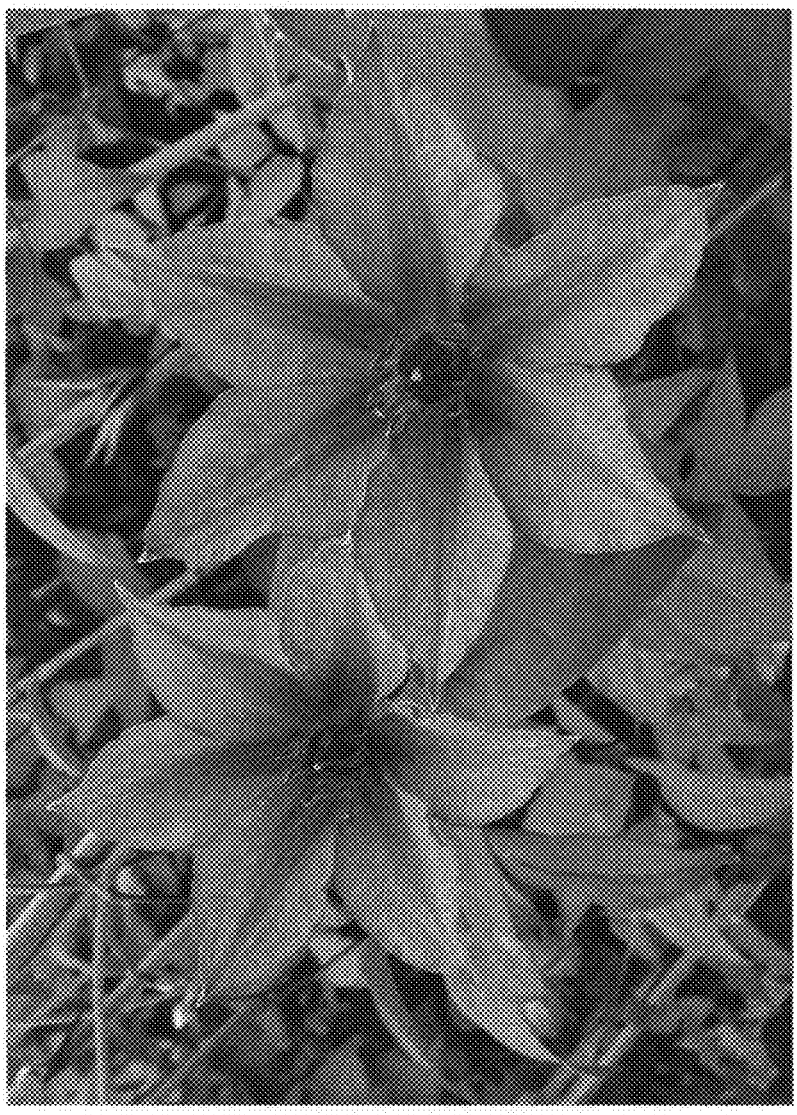

* * * * *